(12) United States Patent
Palma et al.

(10) Patent No.: US 10,755,454 B2
(45) Date of Patent: Aug. 25, 2020

(54) CLINICAL TASK-BASED PROCESSING OF IMAGES

(71) Applicant: General Electric Company, Schenectady, NY (US)

(72) Inventors: Giovanni Palma, Yvelines (FR); Razvan Iordache, Buc (FR); Serge Muller, Buc (FR); Zhijin Li, Buc (FR); Ann-Katherine Carton, Yvelines (FR)

(73) Assignee: General Electric Company, Schenectady, NY (US)

( * ) Notice: Subject to any disclaimer, the term of this patent is extended or adjusted under 35 U.S.C. 154(b) by 206 days.

(21) Appl. No.: 15/852,076

(22) Filed: Dec. 22, 2017

(65) Prior Publication Data
US 2019/0197742 A1    Jun. 27, 2019

(51) Int. Cl.
| | |
|---|---|
| G06K 9/00 | (2006.01) |
| G06T 11/00 | (2006.01) |
| G06T 7/00 | (2017.01) |
| G06K 9/46 | (2006.01) |
| G06T 5/00 | (2006.01) |
| A61B 6/00 | (2006.01) |

(52) U.S. Cl.
CPC .............. *G06T 11/008* (2013.01); *G06K 9/46* (2013.01); *G06T 5/00* (2013.01); *G06T 7/0012* (2013.01); *A61B 6/502* (2013.01); *G06T 2207/10112* (2013.01); *G06T 2207/30068* (2013.01)

(58) Field of Classification Search
CPC .................. G06T 11/008; G06T 7/0012; G06T 2207/10112; G06T 2207/30068; A61B 6/502; G06K 9/46

USPC ......................................................... 382/131
See application file for complete search history.

(56) References Cited

U.S. PATENT DOCUMENTS

| | | | | |
|---|---|---|---|---|
| 7,133,546 | B2 * | 11/2006 | Dehmeshki | G06F 19/321 |
| | | | | 382/128 |
| 10,127,659 | B2 * | 11/2018 | Hsieh | G06T 7/0012 |
| 10,565,477 | B2 * | 2/2020 | Hsieh | G06N 3/0454 |
| 2008/0025583 | A1 | 1/2008 | Jabri | |
| 2009/0268953 | A1 * | 10/2009 | Crucs | A61B 6/583 |
| | | | | 382/128 |

(Continued)

OTHER PUBLICATIONS

EP Patent Application No. 18213158, Extended European Search Report dated Apr. 17, 2019.

*Primary Examiner* — Jonathan S Lee
(74) *Attorney, Agent, or Firm* — Boyle Fredrickson, S.C.

(57) ABSTRACT

An imaging system, such as a DBT system, is provided that is capable of providing processing of an image from initial generation/reconstruction of the image through the review of the image by a radiologist or other practitioner that produces images optimized for the particular task/process performed using the images. The task/review that the radiologist is performing on the processed or reconstructed image can be modeled with regard to the initial generation of the processed or reconstructed images from the raw images or the model considerations can be retroactively applied and back propagated through the image processing performed by the system. These modeling considerations that can take the form of an indicator of clinical performance is/are used by the system to optimize and produce an image(s) that best represents the items in the image necessary for an accurate diagnosis of the patient when reviewed by the radiologist.

17 Claims, 2 Drawing Sheets

(56) References Cited

U.S. PATENT DOCUMENTS

2016/0209995 A1  7/2016  Jeon
2017/0337713 A1  11/2017 Hoelzer

* cited by examiner

CLINICAL TASK-BASED PROCESSING OF IMAGES

BACKGROUND

X-ray screening exams are used to detect breast cancer and other diseases. Efforts to improve the sensitivity and specificity of breast x-ray systems have led to the development of tomosynthesis systems. Breast tomosynthesis is a three-dimensional imaging technology that involves acquiring images of a stationary compressed breast at multiple angles during a short scan. The individual images are reconstructed into a series of thin, high-resolution slices that can be displayed individually or in a dynamic cine mode. Reconstructed tomosynthesis slices reduce or eliminate the problems caused by tissue overlap and structure noise in single slice two-dimensional mammography imaging. Digital breast tomosynthesis also offers the possibility of reduced breast compression, improved diagnostic and screening accuracy, fewer recalls, and 3D lesion localization.

In order to facilitate screening and diagnosis with tomosynthesis systems, such as systems for conducting digital breast tomosynthesis (DBT) or contrast-enhanced digital breast tomosynthesis (CE-DBT) scans or acquisitions, it is generally desirable to obtain high quality images for accurate diagnoses. These images are reconstructed from the raw image data using suitable algorithms that are applied to the raw image data to create three dimensional (3D) slices and volumes of the tissue imaged in the DBT/CE-DBT acquisitions. In DBT/CE-DBT, the reconstruction step is important as it directly impacts the content of the data represented in the slices/volumes reviewed by the radiologist, and therefore the resulting diagnosis.

The currently employed reconstruction algorithms operate to optimize the quality of reconstructed slices produced from the raw image data by reducing noise and mitigating motion and streaking of artifacts in the image data to provide the best quality image/slice/volume possible. However, for the specific clinical task the radiologist is performing using the reconstructed images e.g., the identification of radiological signs within the imaged tissue, the optimized images provided by the algorithms can often clarify the overall images while reducing the visibility and/or ability of the radiological signs to be identified in the images. As such, the optimization provided by the algorithm might not optimize the visibility of required findings for the data that are being reconstructed/processed.

Accordingly, it is desirable to provide an imaging system, such as a DBT system, with an algorithm or other image processing features that models and/or optimizes the reconstructed images for the particular clinical task being performed by the radiologist viewing the images to improve the ease and accuracy of the diagnoses produced.

BRIEF DESCRIPTION

There is a need or desire for an imaging system, such as a DBT/CE-DBT system, capable of providing processing of an image from initial generation/reconstruction of the image through the review of the image by a radiologist or other practitioner that produces images optimized for the particular task/process performed using the images. The task/review that the radiologist is performing on the reconstructed image can be modeled with regard to the initial generation of the reconstructed images or the model considerations can be retroactively applied and back propagated through the image reconstruction process performed by the system. These modeling considerations that can take the form of indicators of clinical performance are used by the system to optimize and produce an image(s) that best represents the items in the image necessary for an accurate diagnosis of the patient when reviewed by the radiologist.

According to one aspect of the present disclosure, the imaging system enables the tailoring of the presentation of the reconstructed images produced by the system performance for an individual radiologist. The imaging system can anticipate how the radiologist will read an image based on considerations provided by the radiologist and/or past modifications to images required by the radiologist in order to present a reconstructed image utilizing these personalized considerations and/or modifications that will best allow the radiologist to detect the areas of suspicion located within the displayed image(s).

According to another aspect of the present disclosure, a method for enhancing the probability of detection of features of interest within processed images is provided including the steps of providing an imaging apparatus having an image acquisition mechanism that generates a plurality of projections of an imaging target of an object or body in a time series during a scan and an image processor configured to process the plurality of projections to generate processed images, wherein the processed images are generated by the image processor with reference to an indicator of clinical performance providing desired parameters for the processed images to enhance the probability of detecting features of interest within the processed images, and wherein the image processor is configured to produce the processed images from the plurality of projections to optimize the desired parameters provided by the indicator of clinical performance, determining the processed image parameters of the indicator of clinical performance and generating the processed images from the plurality of projections to optimize the processed image parameters from the indicator of clinical performance.

According to still another aspect of the present disclosure, an imaging apparatus is provided that includes an image acquisition mechanism that generates a plurality of projections of an imaging target of an object or body in a time series during a scan and an image processor configured to process the plurality of projections to generate processed images, wherein the processed images are generated by the image processor with reference to an indicator of clinical performance providing desired parameters for the processed images to enhance the probability of detecting features of interest within the processed images, and wherein the image processor is configured to produce the processed images from the plurality of projections to optimize the desired parameters provided by the indicator of clinical performance.

According to another aspect of the present disclosure, a method for maximizing an indicator of clinical performance with regard to features of interest within one or more processed images is provided including the steps of providing an image processor configured to process raw image data to generate the one or more processed images, wherein the one or more processed images are generated by the image processor with reference to at least one indicator of clinical performance providing desired parameters for the processed images to maximize the at least one indicator of clinical performance within the one or more processed images, determining the processed image parameter of the indicator of clinical performance and generating the one or more processed images from the raw image data to optimize the processed image parameters from the at least one indicator of clinical performance.

An imaging processing apparatus including a memory unit adapted to be operably connected to an image data provider to receive image data therefrom, the memory unit configured to receive the image data and at least one indicator of clinical performance and an image processor operably connected to the memory unit and configured to generate a processed image from the image data, wherein the characteristics of the processed image are tuned to maximize the at least one indicator of clinical performance.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings.

DETAILED DESCRIPTION OF THE DRAWINGS

In the following detailed description, reference is made to the accompanying drawings that form a part hereof, and in which is shown by way of illustrations of specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
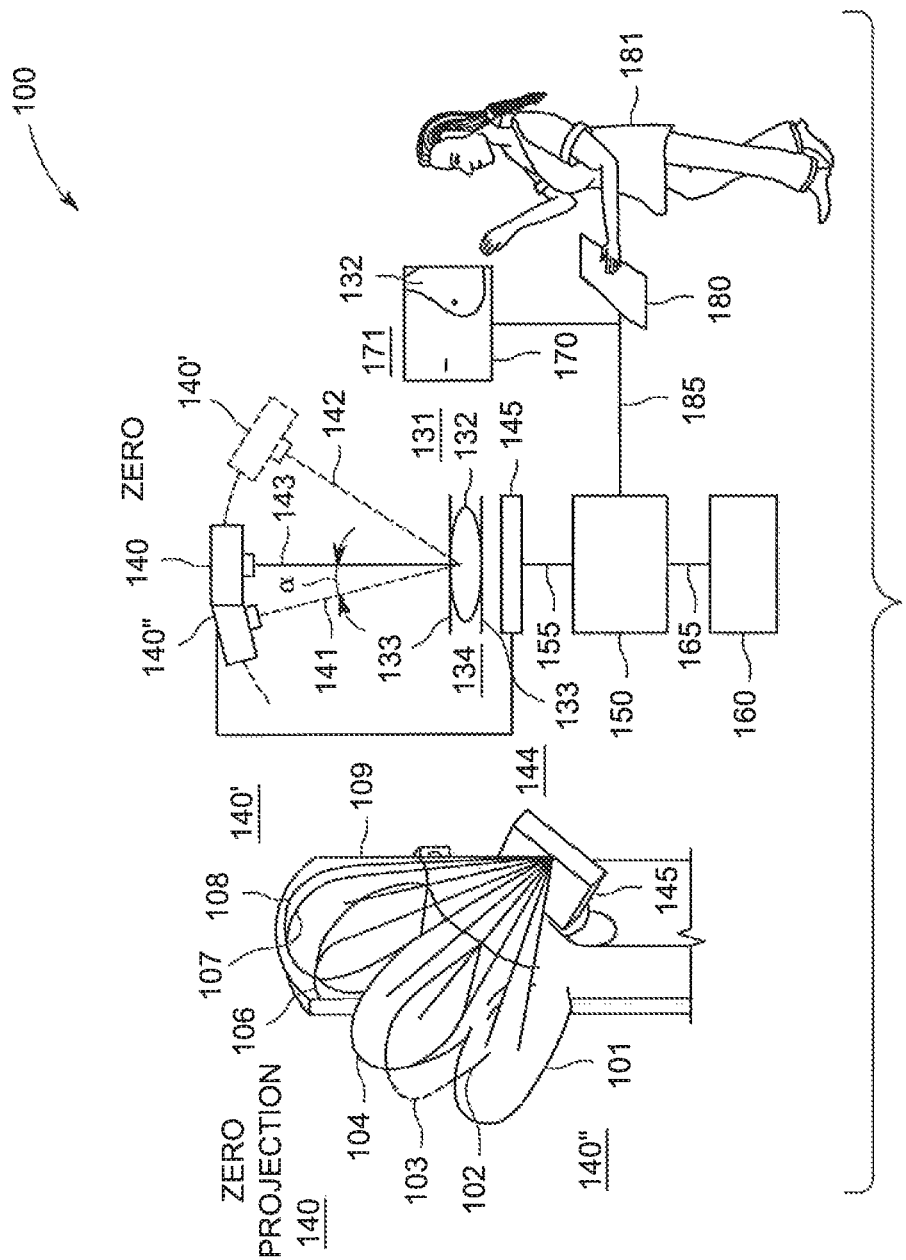
FIG. 1 is a schematic view of an imaging system performing a scan of a patient to determine the presence of an object of interest within the patient according to an exemplary non-limiting embodiment of the present disclosure.

FIG. 1 is a diagrammatic illustration 1 of a mechanism or system for obtaining an enhanced projection image of an object of interest, an example of which is the Senograph Pristina 3D, manufactured by GE Healthcare, wherein the system 100 comprises an x-ray beam source 140 facing the detector 145. The x-ray beam source 140 and the detector 145 are connected by an arm 144. Between the detector 145 and the source 140 an object of interest 132 can be placed. In the system illustrated, the x-ray source 140 moves in an arc above a single detector 145. The detector 145 and a plurality of positions of the x-ray source 140' and 140" following an arc (see dashed line) are shown with dashed/solid lines and in a perspective partial view. In the shown arrangement, the detector 145 is fixed at the shown position and only the x-ray source 140 moves. The angle α is a projection angle enclosed by the zero-orientation and any other orientation such as 141 and 142. In this way, multiple different views of the breast tissue can be acquired via at least one x-ray source 140. The projection of lowest α or the projection closest to the zero-orientation is named the central projection or zero projection by approximation.

Still referring to FIG. 1, on the left side is shown a partial perspective view of an imaging system according to an exemplary non-limiting embodiment of this disclosure comprising a detector 145 and an x-ray source 140. The different positions of the x-ray source 140, 140' and 140" are broadly depicted to illustrate the movement of the x-ray source. There are nine different projection views 101, 102, 102, 103, 104, 106, 107, 108, 109 including the zero projection (143) indicated as straight lines, which all point to the center of the detector 145.

The patient (not shown) is positioned in front of the mammography arm. To take for example a known mediolateral oblique (MLO) view, the mammography technologist 181 will set the angle for the desired projection (30 degrees to 60 degrees, wherein 45 degree represents the preferred zero projection shown in the perspective view of FIG. 1). During routine screening mammography, the angled MLO view is preferred over a lateral 90-degree projection because more of the breast tissue can be imaged.

The object of interest 132 shown in display unit 170 is a breast compressed by compression paddles 133, which ensure uniform compression and immobilization of the breast during the radiation exposure for optimal image quality. The breast 132 comprises for example a punctual object 131 as a calcification, which is located in the zero orientation 143, which is perpendicular to the detector 145 plane. The user may review calcifications or other clinical relevant structures for diagnosis. The display depicts a known 2D mammography view, where mainly the middle portion of the breast 132 can be reviewed.

The detector 145 and the x-ray source 140 constitute the acquisition unit, which is connected via a data acquisition line 155 to a computer/image processing unit 150. The processing unit 150 comprises a memory unit 160, which may be connected via an archive line 165.

A user such as a health professional may input control signals via the user interface 180. Such signals are transferred from the user interface to the processing unit 150 via the signal line 185. The method and system according to the disclosure enables the user to obtain an enhanced 2D projection image that looks like a known 2D mammogram. Based on this high quality image, the radiologist is capable of identifying all the clinical signs relevant for breast screening. Especially if the health professional is used to known 2D mammograms, the user may easily analyze the displayed picture. Further there is the possibility of displaying stored former 2D mammograms for comparison with the one acquired. Besides, tomosynthesis images may be reviewed and archived. A CAD system or the user himself can provide 3D marks. A height map of punctual objects or other objects obtained according to an embodiment of the disclosure can be combined with height information provided by 3D marks by a CAD system or indicated by a user through a 3D review system. Further, the user may decide if the 2D full-volume images or other images are archived or not. Alternatively saving and storing of the images may be done automatically.

The memory unit 160 can be integral or separate from the processing unit 150. The memory unit 160 allows storage of data such as the 2D enhanced projection image and optionally tomosynthesis 3D images. In general, the memory unit 160 may comprise a computer-readable medium for example a hard disk or a CD-ROM, diskette, a ROM/RAM memory, DVD, a digital source such as a network or the Internet or any other suitable means. The processing unit 150 is configured to execute program instructions stored in the memory unit 160, which cause the computer to perform the methods of the disclosure. One technical effect of performing the method according to the embodiments of the present disclosure is that the x-ray source may be less used, since the enhanced 2D projection image can replace a known 2D mammogram, which usually is based on a separate x-ray exposure in order to get high quality images.

Figure 2:
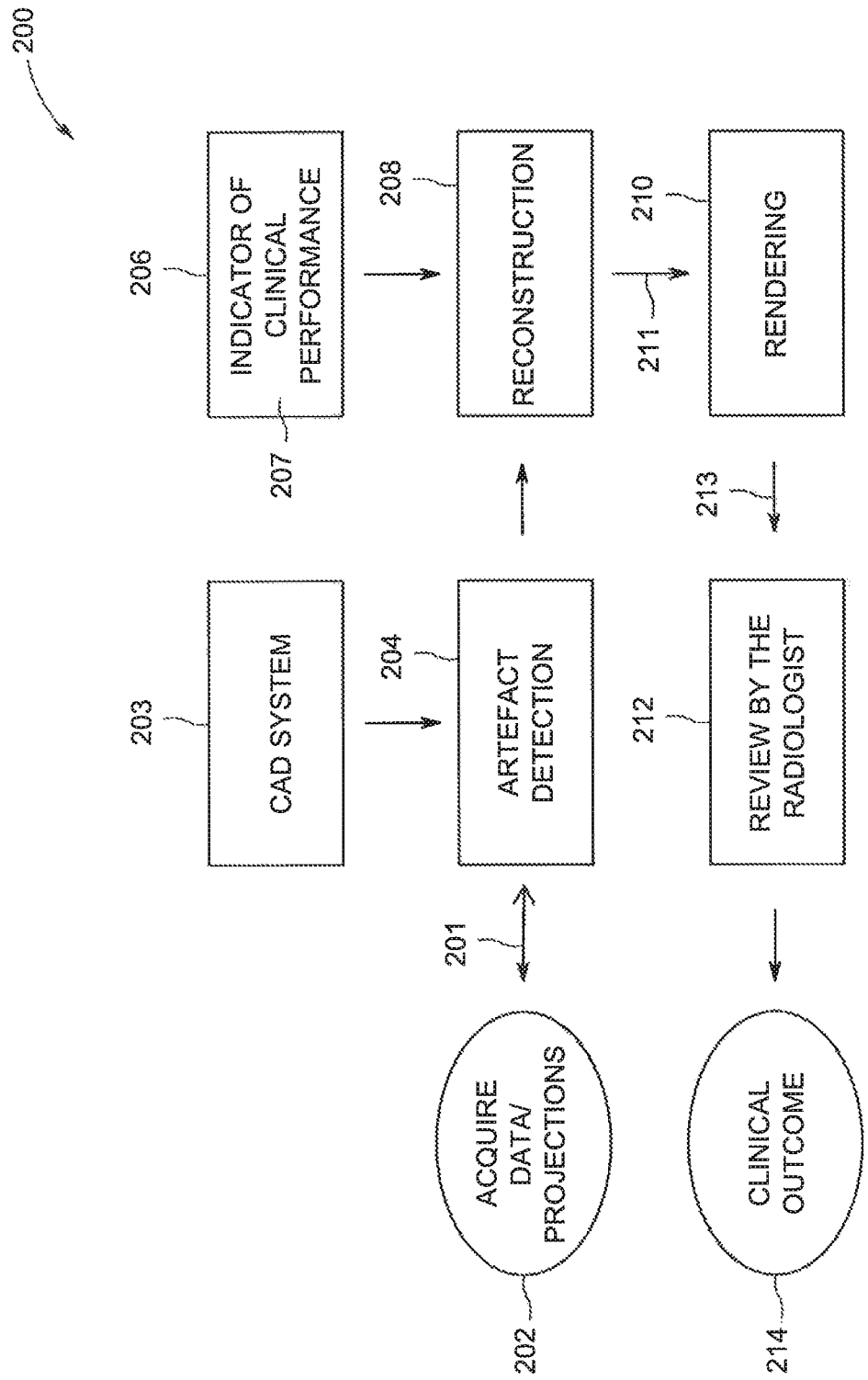
FIG. 2 is a schematic view of a method for optimizing the images for display of features of interest within the images according to an exemplary non-limiting embodiment of the present disclosure.

Referring now to the exemplary non-limiting embodiment of the operation of the system 100 in FIG. 2, in the method 200 the system 100 initially obtains the raw image data/ projections 201 at each point where the source 140 has been operated in step 202. Alternatively, the system 100 can obtain the raw image data and store the raw image data in a database (not shown) also operably connected to the system 100, which may be a part of the image system 100 or a separate component therefrom.

In subsequent step 204, the processing unit/image processor 150, which can be formed as the same component of the system 100 or as different but interconnected components, such as a separate system operably connected to the raw image data database, e.g., a PACS database, analyzes the projections 201 or any data derived from the projections 201 to determine the presence of any areas or features of interest/artefacts 131, such as calcifications, within the projections 201. This analysis can be performed using a computer-aided detection (CAD) system 203 contained within and/or operably connected to the system 100 and image processor 150. The CAD system 203 identifies and marks the features of interest 131 within the raw images/projections 201 in any suitable manner, such as by searching for clusters of bright spots (not shown) in the projections 201.

After detection of the features of interest 131 within the projections, in step 206 the system 100, and in particular the image processor 150, determines what indicator(s) of clinical performance 207 has been input to the system 100 by the radiologist or other practitioner via the interface 180, and optionally stored in the memory unit 160. The indicator(s) 207 identify the particular review of the reconstructed images 211 and/or the features of interest 131 that are the subject of that review which is to be performed by the radiologist to provide the diagnosis of the imaged tissue. With the indicator 207, the image processor 150 can determine the optimal image parameters for the display or presentation of the features of interest 131 in the reconstructed images/slices/volumes 211 to be created by the image processor 150 in order to facilitate the review of the images 211. In one exemplary non-limiting embodiment, when the indicator 207 identifies calcifications as the features of interest 131, the normal settings for a contrast to nice ratio utilized to optimize the clarity of the overall reconstructed images/slices/volumes can be adjusted to a different contrast ratio that maximizes the display of any calcifications within the reconstructed images, with a corresponding sacrifice in the overall sharpness or clarity of the reconstructed image. The indicator 207 can have various forms, and in certain exemplary non-limiting embodiments the indicator 207 can be or include at least one parameter to enhance the detection of features of interest within the processed images, at least one parameter to enhance the characterization of the features of interest within the processed images, at least one parameter to enhance a task to be performed on the processed images by the image processor, at least one parameter to enhance a task to be performed on the processed images by an operator of the apparatus during clinical assessment, and combinations thereof.

After determination of the location of one or more features of interest 205 in the projections 201, and the analysis of the indicator of clinical performance 207, in step 208 the imaging processor 150 receives the raw image data and/or projections 201 including the identification of the artefacts/ features of interest 131 therein, and employs a suitable processing and/or reconstruction algorithm 209 in order to process the raw image data/one or more projections from the detector 145 obtained at each point where the source 140 has been operated, which can be at one or more points relative to the detector 145. With regard to the processing provided by the image processor 150 on the raw image data/projections 201, the processing is can be selected from DBT reconstruction, CT reconstruction, CE-DBT reconstruction, dual energy recombination (CESM) and 2D processing, among other suitable image processing and/or reconstruction procedures. Further, the particular algorithm utilized can be selected from any suitable algorithm, such as a Fourier-domain reconstruction algorithm, a back projection algorithm, an iterative reconstruction algorithm, and a fan beam algorithm, and in the illustrated exemplary non-limiting embodiment the reconstruction algorithm takes the following generalized form:

$$\text{Arg min } v(\|AV-P\|+\text{aPriori}(V))$$

where A is the system geometry; V is the volume to be reconstructed and P is/are the acquired projections. Using this algorithm, the image processor 150 reconstructs a number of volume and/or slices 211 of the imaged tissue.

Further, in the reconstruction process, the resulting images/slices/volumes 211 are analyzed by the image processor 150 with respect to the indicator 207 previously determined in step 206. In this analysis, the image processor 150 looks through the different images/slices/volumes 211 to maximize the image parameters provided by the indicator 207. In doing so, the indicator 207 provides guidelines to the image processor 150 for the parameters to be optimized in the resulting construction of reconstructed images/slices/ volumes 211 that are best suited for the display and detection of the features of interest 131 within the images/slices/ volumes 211. Thus, using the indicator 207 the image processor 150 constructs reconstructed images/slices/volumes 211 from the projections 201 that best fit the parameters for those images meeting the image criteria identified by the indicator 207, e.g., altered contrast to noise ratios. In employing the exemplary algorithm above in conjunction with the indicator 207, the reconstruction can be performed to provide images/slices/volumes 211 which are best fits of the L2 norm to minimize the distance between the data present in the raw projections from the corresponding location in the reconstructed images/slices/volumes 211. In this manner, the reconstructed images/slices/volumes 211 are optimized to provide accurate locations of the features of interest 131 within the images/slices/volumes 211 along with the desired resolution or quality/sharpness of the reconstructed images/slices/volumes 211 to maximize the detection of the features of interest 131.

Further, within the set of reconstructed images/slices/ volumes 211 formed by the image processor 150 in this manner, the best image/slice/volume 211 can be determined and/or selected for display to the radiologist. To optionally assist in making this determination, either after or as an addition/complement to the reconstruction step 208, the system 100 moves to step 210 where the reconstructed images/slices/volume 211 is/are contrast-enhanced utilizing a suitable rendering algorithm and/or by enhancing certain areas of the reconstructed images using, for example, an output look up table and/or interpolation, among other acceptable formats, or according to the following exemplary algorithm:

$$\text{Arg min}_V(\|AV-P\|+\text{aPriori}(V)+\text{indicator(rendering}(V)))$$

where A is the system geometry. V is the volume to be reconstructed, P is/are the acquired projections and the rendering algorithm is modified using the image parameters provided by the indicator 207.

In an exemplary non-limiting embodiment, in this step 210 the image processor 150 provides enhancement to one or more features of interest or artefacts 131 within the images/slices/volume 211 in order to enable a radiologist/practitioner to more readily distinguish the feature of interest 131 within the reconstructed image/slice/volume 211.

Post-rendering, the reconstructed and enhanced image(s)/slice(s)/volume(s) 213 is presented and reviewed by the radiologist in step 212 such that the radiologist can provide the clinical outcome/diagnosis in block 214.

In another exemplary non-limiting embodiment of the system 100 and associated method 200, for various reasons including the testing of the image processor 150 with regard to certain particular features of interest 131, step 204 can be re-tasked by employing a set of simulated or phantom features 131 that are positioned in the projections 201 by the image processor 150. These projections 201 including the simulated features 131 are then subjected to the remainder of the steps 206-214 in the method 200. This optimization for these simulated features 131 using the appropriate indicator 207 also provide the same enhancements to actual but unknown or undetected features 131 in the reconstructed images/slices/volumes 211, resulting in the higher probability of display of the actual features 131 for detection when displayed. With the operation of the system 100 and the method 200, one technical effect is the ability to tailor the performance of a radiologist for a given patient by using information provided on the type(s) of lesions/features 131 sought within the projections 201 to enhance the display of the features 131 within an optimized reconstructed image 211 to enhance the detection of features of interest 131 within the one or more processed images 211, to enhance the characterization of the features of interest 131 within the one or more processed images 211, to enhance a task to be performed on the processed images 211 by the image processor 150, to enhance a task to be performed on the processed images 211 by an operator of the system 100 during clinical assessment, and combinations thereof.

In another exemplary non-limiting embodiment of the system 100 and associated method 200, the selection of the "best" reconstructed image/slice/volume 211 is performed by defining an energy to minimize composed of a weighted sum of a first term of data fidelity and a second term related to the indicator 207. With such a modeling, the solution is no more defined as the one that perfectly matches the data and at the same time maximizes the clinical performance assessed by the indicator 207. It is rather a balance between both data fit and clinical performance. Therefore, depending on the weight, the solution for the best image 211 can be biased toward a less accurate and but more clinically relevant one/image. In an exemplary non-limiting embodiment, a non-crisp CAD output, such as image including a probability of detection or other values derived from any other mathematical framework, could be used and be used within this energy to be minimized in addition to the mathematical model of the detection task to be performed by the radiologist on the rendered image.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An imaging processing apparatus comprising:
   a memory unit adapted to be operably connected to an image data provider to receive image data therefrom, the memory unit configured to receive the image data and at least one indicator of clinical performance input by a user; and
   an image processor operably connected to the memory unit and configured to generate a processed image from the image data, wherein the characteristics of the processed image generated by the image processor from raw image data are tuned to maximize the at least one indicator of clinical performance stored in the memory unit,
   wherein the at least one indicator of clinical performance comprises image parameters for the modification of at least one of the enhancement of the detection of features of interest, enhancement of the characterization of the features of interest, enhancement of an image evaluation task to be performed by the image processor, enhancement of an image evaluation task to be performed by the reader during clinical assessment, and combinations thereof.

2. The apparatus of claim 1, wherein the image data provider is an imaging system including an x-ray source and a detector operably connected to the memory unit and the image processor that generates the image data of an imaging target of an object or body.

3. The apparatus of claim 1, wherein the apparatus further comprises a detection system for detecting the features of interest within the image dataset.

4. The apparatus of claim 3, wherein the detection system is a computer-aided detection system.

5. The apparatus of claim 3, wherein the features of interest are phantom features inserted within the processed image.

6. The apparatus of claim 1, wherein the image processor generates the processed images from the image data using a processing mode selected from the group consisting of: DBT reconstruction, CT reconstruction, CE-DBT reconstruction, dual energy recombination (CESM) and two or three dimensional post-processing.

7. The apparatus of claim 1, wherein the image processor is configured to alter the processing of or select a processed image among the image data that maximizes the at least one indicator of clinical performance.

8. The apparatus of claim 1, wherein the parameters provided by the indicator of clinical performance differ from general processed image qualities stored in the image processor.

9. The apparatus of claim 1, wherein the parameters provided by the indicator of clinical performance include a weighting factor relating to a probability of detection of the features of interest present within the processed images.

10. A method for maximizing an indicator of clinical performance with regard to features of interest within one or more processed images, the method comprising the steps of:
providing an image processor configured to process raw image data to generate the one or more processed images, wherein the one or more processed images are generated by the image processor with reference to at least one indicator of clinical performance input to the image processor by the user and providing desired image parameters for the processed images to maximize the at least one indicator of clinical performance within the one or more processed images;
determining the processed image parameter of the indicator of clinical performance; and
generating the one or more processed images from the raw image data to optimize the processed image parameters from the at least one indicator of clinical performance.

11. The method of claim 10, wherein the imaging apparatus includes a detection system for detecting features of interest within the processed images and further comprising the step of detecting any features of interest within the raw image data prior to generating the one or more processed images.

12. The method of claim 11, wherein the step of detecting the features of interested within the raw image data comprises inserting phantom features within the raw image data.

13. The method of claim 10, wherein the image processor includes an image acquisition system for acquiring the raw image data supplied to the image processor, and further comprising the step of operating the image acquisition system to acquire the raw image data.

14. The method of claim 10, further comprising the step of selecting a best optimized processed image for review.

15. The method of claim 10, wherein the image processor generates the one or more processed images from the raw image data using a processing mode selected from the group consisting of: DBT reconstruction, CT reconstruction, CE-DBT reconstruction, dual energy recombination (CESM) and two dimensional processing.

16. The method of claim 10, wherein the indicator of clinical performance is selected from the group consisting of: at least one parameter to enhance the detection of features of interest within the processed images, at least one parameter to enhance the characterization of the features of interest within the processed images, at least one parameter to enhance a task to be performed on the processed images by the image processor, at least one parameter to enhance a task to be performed on the processed images by an operator of the apparatus, and combinations thereof.

17. The method of claim 16, wherein the parameters provided by the indicator of clinical performance include a weighting factor relating to a probability of detection of the features of interest present within the processed images.

* * * * *